(12) United States Patent
Wilson et al.

(10) Patent No.: US 9,220,424 B2
(45) Date of Patent: Dec. 29, 2015

(54) SYSTEM AND METHOD FOR MEASURING THE PRESSURE OF A FLUID SYSTEM WITHIN A PATIENT

(75) Inventors: Stephen F. Wilson, Easton, MA (US); Alan J. Dextradeur, Franklin, MA (US)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

(21) Appl. No.: 12/496,871

(22) Filed: Jul. 2, 2009

(65) Prior Publication Data

US 2009/0270759 A1    Oct. 29, 2009

Related U.S. Application Data

(62) Division of application No. 11/025,683, filed on Dec. 29, 2004, now Pat. No. 7,585,280.

(51) Int. Cl.
*A61B 5/03* (2006.01)
*A61B 19/00* (2006.01)

(52) U.S. Cl.
CPC ........... *A61B 5/032* (2013.01); *A61B 2019/464* (2013.01); *A61M 2202/0464* (2013.01)

(58) Field of Classification Search
USPC .......... 600/561, 300, 555, 560, 587; 604/8, 9; 702/138, 139, 140
See application file for complete search history.

(56) References Cited

U.S. PATENT DOCUMENTS

| | | |
|---|---|---|
| 2,396,351 A | 3/1946 | Thompson |
| 3,757,770 A * | 9/1973 | Brayshaw et al. ............ 600/302 |
| 3,886,948 A | 6/1975 | Hakim |
| 3,960,142 A | 6/1976 | Elliott et al. |
| 3,976,278 A | 8/1976 | Dye et al. |
| 4,077,882 A | 3/1978 | Gangemi |
| 4,114,603 A * | 9/1978 | Wilkinson ................... 600/561 |
| 4,135,509 A | 1/1979 | Shannon |
| 4,332,255 A | 6/1982 | Hakim et al. |
| 4,387,715 A | 6/1983 | Hakim et al. |
| 4,421,124 A | 12/1983 | Marshall |

(Continued)

FOREIGN PATENT DOCUMENTS

| | | |
|---|---|---|
| AU | 729 467 B2 | 2/2001 |
| EP | 1676527 A1 * | 7/2006 |

(Continued)

OTHER PUBLICATIONS

Ekstedt, J., "CSFS Hydrodynamic Studies in Man, 1. Method of Constant Pressure CSF Infusion", J. Neurology, Neurosurgery & Psych. 40:105-19 (1977).

(Continued)

*Primary Examiner* — Sean Dougherty
(74) *Attorney, Agent, or Firm* — Nutter McClennen & Fish LLP

(57) ABSTRACT

A pressure sensing apparatus has a pressure sensor component that includes a pressure sensing port, a pressure sensor for sensing a pressure of a fluid in the pressure sensing port, and a digital processor communicating with the pressure sensor for performing calculations involving fluid pressures sensed. The pressure sensing apparatus further includes a first chamber in fluid contact with the pressure sensing port, a second chamber fluidically connectable with a patient's cerebrospinal fluid system, and a membrane located between the first and second chambers so as to transmit fluid pressure from the second chamber to the first chamber.

26 Claims, 4 Drawing Sheets

(56) References Cited

U.S. PATENT DOCUMENTS

| | | | |
|---|---|---|---|
| 4,551,128 A | 11/1985 | Hakim et al. | |
| 4,556,086 A | 12/1985 | Raines | |
| 4,576,181 A | 3/1986 | Wallace et al. | |
| 4,595,390 A | 6/1986 | Hakim et al. | |
| 4,615,691 A | 10/1986 | Hakim et al. | |
| 4,711,249 A | 12/1987 | Brooks | |
| 4,727,887 A | 3/1988 | Haber | |
| 4,772,257 A | 9/1988 | Hakim et al. | |
| 4,820,265 A | 4/1989 | DeSatnick et al. | |
| 4,893,630 A | 1/1990 | Bray, Jr. | |
| 5,004,472 A | 4/1991 | Wallace | |
| 5,009,662 A | 4/1991 | Wallace et al. | |
| 5,021,046 A | 6/1991 | Wallace | |
| 5,163,904 A | 11/1992 | Lampropoulos et al. | |
| 5,201,753 A | 4/1993 | Lampropoulos et al. | |
| 5,280,789 A | 1/1994 | Potts | |
| 5,337,612 A | 8/1994 | Evans | |
| 5,396,899 A | 3/1995 | Strittmatter | |
| 5,425,713 A | 6/1995 | Taylor et al. | |
| 5,431,629 A | 7/1995 | Lampropoulos et al. | |
| 5,449,345 A | 9/1995 | Taylor et al. | |
| 5,490,514 A | 2/1996 | Rosenberg | |
| 5,591,171 A | 1/1997 | Brown | |
| 5,622,869 A | 4/1997 | Lewis et al. | |
| 5,704,352 A * | 1/1998 | Tremblay et al. | 600/300 |
| 5,711,302 A | 1/1998 | Lampropoulos et al. | |
| 5,716,342 A | 2/1998 | Dumbraveanu et al. | |
| 5,721,382 A | 2/1998 | Kriesel et al. | |
| 5,785,822 A | 7/1998 | Cerri et al. | |
| 5,797,403 A | 8/1998 | DiLorenzo | |
| 5,803,917 A | 9/1998 | Butterfield et al. | |
| 5,928,182 A | 7/1999 | Kraus et al. | |
| 5,935,083 A | 8/1999 | Williams | |
| 5,970,801 A | 10/1999 | Ciobanu et al. | |
| 5,993,395 A | 11/1999 | Shulze | |
| 5,993,398 A * | 11/1999 | Alperin | 600/561 |
| 6,010,482 A | 1/2000 | Kriesel et al. | |
| 6,071,267 A | 6/2000 | Zamierowski | |
| 6,113,553 A * | 9/2000 | Chubbuck | 600/561 |
| 6,158,965 A | 12/2000 | Butterfield et al. | |
| 6,171,252 B1 | 1/2001 | Roberts | |
| 6,416,291 B1 | 7/2002 | Butterfield et al. | |
| 6,432,050 B1 * | 8/2002 | Porat et al. | 600/300 |
| 6,470,213 B1 | 10/2002 | Alley | |
| 6,475,147 B1 * | 11/2002 | Yost et al. | 600/438 |
| 6,481,292 B1 | 11/2002 | Reich | |
| 6,503,208 B1 | 1/2003 | Skovlund | |
| 6,533,733 B1 * | 3/2003 | Ericson et al. | 600/561 |
| 6,589,189 B2 | 7/2003 | Meyerson et al. | |
| 7,014,624 B2 * | 3/2006 | Meythaler et al. | 604/113 |
| 2003/0023134 A1 | 1/2003 | Tracey | |

FOREIGN PATENT DOCUMENTS

| | | | |
|---|---|---|---|
| JP | 59-144438 | 8/1984 | |
| JP | 11299742 A * | 11/1999 | A61B 5/00 |
| JP | 2006187621 A * | 7/2006 | |
| WO | WO 2007014582 A1 * | 2/2007 | A61M 1/00 |

OTHER PUBLICATIONS

European Search Report, Appl. No. 052580800.0, dated May 15, 2006.

Shapiro, K. et al.: "Characterization of Clinical CSF Dynamics and Neural Axis Compliance Using the Pressure-Volume Index: I. The Normal Pressure-Volume Index", Annals of Neurology, 7(6):508-14 (1980).

"User's Manual HD2114.0-HD2134.0, HD2164.0-HD2114B.0, HD2114, 2-HD2134.2, HD2164.2-HD2114B.2; Rev. 1.0", Delta OHM, via G. Marconi, 5-35020 Caselle Di Selvazzano(PD)—Italy, pp. 2-6 (Oct. 1, 2004).

* cited by examiner

SYSTEM AND METHOD FOR MEASURING THE PRESSURE OF A FLUID SYSTEM WITHIN A PATIENT

RELATED APPLICATIONS

This application is a divisional of U.S. patent application Ser. No. 11/025,683, filed Dec. 29, 2004, and entitled "System and Method for measuring the Pressure of a Fluid System Within a Patient," which application is incorporated by reference herein.

BACKGROUND OF THE INVENTION

Cerebrospinal fluid, typically abbreviated as CSF, is a fluid that protects the brain and spine and helps distribute nutrients to these structures. CSF is a clear, colorless fluid that is primarily produced by the choroid plexus and surrounds the brain and spinal cord. Hydrocephalus is a condition in which a patient accumulates an excess volume of CSF. This often results from an obstruction of the cerebrospinal fluid pathways or from an inability to absorb the necessary volume of CSF. Increased CSF production relative to absorption causes the ventricles to become wider or dilate to make room for the extra fluid. Hydrocephalus is usually accompanied by an increase in CSF pressure which can be measured with a spinal tap, also known as a lumbar puncture. A spinal tap is a procedure in which a needle is inserted into a space inside the spinal canal for the purpose of removing some of the CSF.

The treatment of hydrocephalus has conventionally involved draining the excess fluid away from the ventricles and rerouting the cerebrospinal fluid to another area of the patient's body, such as the peritoneal cavity. A drainage system, commonly referred to as a shunt, is often used to carry out the transfer of fluid. In order to install the shunt, typically a scalp incision is made and a small hole is drilled in the skull. A proximal, or ventricular, catheter is installed in the ventricular cavity of the patient's brain, while a distal, or drainage, catheter is installed in that portion of the patient's body where the excess fluid is to be reintroduced. Generally, the shunt systems include a valve mechanism that operates to permit fluid flow only once the fluid pressure reaches a certain threshold level. That is, fluid flows through the valve only when the fluid pressure overcomes the valve mechanism's resistance to open. Some valve mechanisms permit the adjustment, or programming, of the opening pressure level, or resistance level, at which fluid flow commences. These valve mechanisms can comprise a variety of configurations. For example, the valve mechanism can be configured as a ball-in-cone as illustrated and described in U.S. Pat. Nos. 3,886,948, 4,332,255, 4,387,715, 4,551,128, 4,595,390, 4,615,691, 4,772,257, and 5,928,182, all of which are hereby incorporated by reference.

In some cases, however, hydrocephalus is characterized by an increase in the volume of CSF and a dilating of the ventricles with only slight or no increase in CSF pressure. This condition is known as normal pressure hydrocephalus. Even without an abnormal increase in CSF pressure, the widening of the ventricles to make room for excess CSF volume can have a deleterious impact on certain brain structures.

Normal pressure hydrocephalus can be difficult to diagnose. In part, the condition is difficult to diagnose because tests used to scan inside the brain, such as CT or MRI imaging, do not show a pattern that definitively indicates that a patient's condition is normal pressure hydrocephalus. A classic triad of symptoms (gait disorder, dementia, and incontinence) is also used in normal pressure hydrocephalus diagnosis. CSF pressure dynamics assessment can also be used, however, there is no convenient equipment for tracking and analyzing CSF pressure over time or measuring its response to stimulus. Once diagnosed, normal pressure hydrocephalus can be treated with shunting generally as described above.

SUMMARY OF THE INVENTION

The present invention provides a pressure sensor with integrated fluid dynamics assessment that can be coupled with a patient's fluid system, for example a patient's CSF system, to measure and analyze the patient's CSF pressure, as well as methods for doing the same. The invention can be used to diagnose a variety of conditions, especially, but not limited to, normal pressure hydrocephalus, and can further be used to aid in treatment, helping to determine for example the appropriate pressure characteristics of a shunt to be used in the treatment.

In a first aspect, the invention provides a pressure sensing apparatus having a pressure sensor component. The pressure sensor component includes a pressure sensing port, a pressure sensor for sensing a pressure of a fluid in the pressure sensing port, and a digital processor communicating with the pressure sensor for performing calculations involving fluid pressures sensed. The pressure sensing apparatus further includes a first chamber in fluid contact with the pressure sensing port, a second chamber fluidically connectable with a patient's cerebrospinal fluid system, and a membrane located between the first and second chambers so as to transmit fluid pressure from the second chamber to the first chamber.

In certain embodiments, the tube can be configured to be connected to a patient's cerebrospinal fluid system through a lumbar tap. The apparatus can also include a bolus apparatus, such as a three way stopcock located between a patient connecting end of the tube and the second chamber with the three way stopcock including a port through which a fluid may inserted or withdrawn, for example, using a syringe.

In still further embodiments, the pressure sensor component includes a display that can be configured to display a graph of fluid pressures sensed over time. The pressure sensor component can further be configured to calculate a resting pressure, an output resistance, and/or a pressure volume index based on fluid pressures measured. The pressure sensor component can also be an integrated, hand-held unit.

In another aspect, the invention provides a pressure sensor component including a pressure sensing port for containing a fluid for pressure sensing, a pressure sensor for measuring a pressure of a fluid in the pressure sensing port, and a processor in electrical communication with the pressure sensor. The processor is configured to calculate at least one selected from the group consisting of resting pressure, outflow resistance, and pressure volume index based on fluid pressure measured by the pressure sensor.

In a further aspect, the invention includes a method for measuring a pressure of a cerebrospinal fluid system in a patient using a pressure sensing system having sterile portion for connecting to a patient's cerebrospinal fluid system and a non-sterile portion including a pressure sensor component having a pressure sensor and a processor for analyzing cerebrospinal fluid pressures measured by the pressure sensor. The method further includes connecting the non-sterile portion to the patient's cerebrospinal fluid system and measuring and displaying the patient's cerebrospinal fluid pressure on the pressure sensor component.

BRIEF DESCRIPTION OF THE DRAWINGS

The invention will be more fully understood from the following detailed description taken in conjunction with the accompanying drawings, in which.

DETAILED DESCRIPTION OF THE PREFERRED EMBODIMENTS

Figure 1:
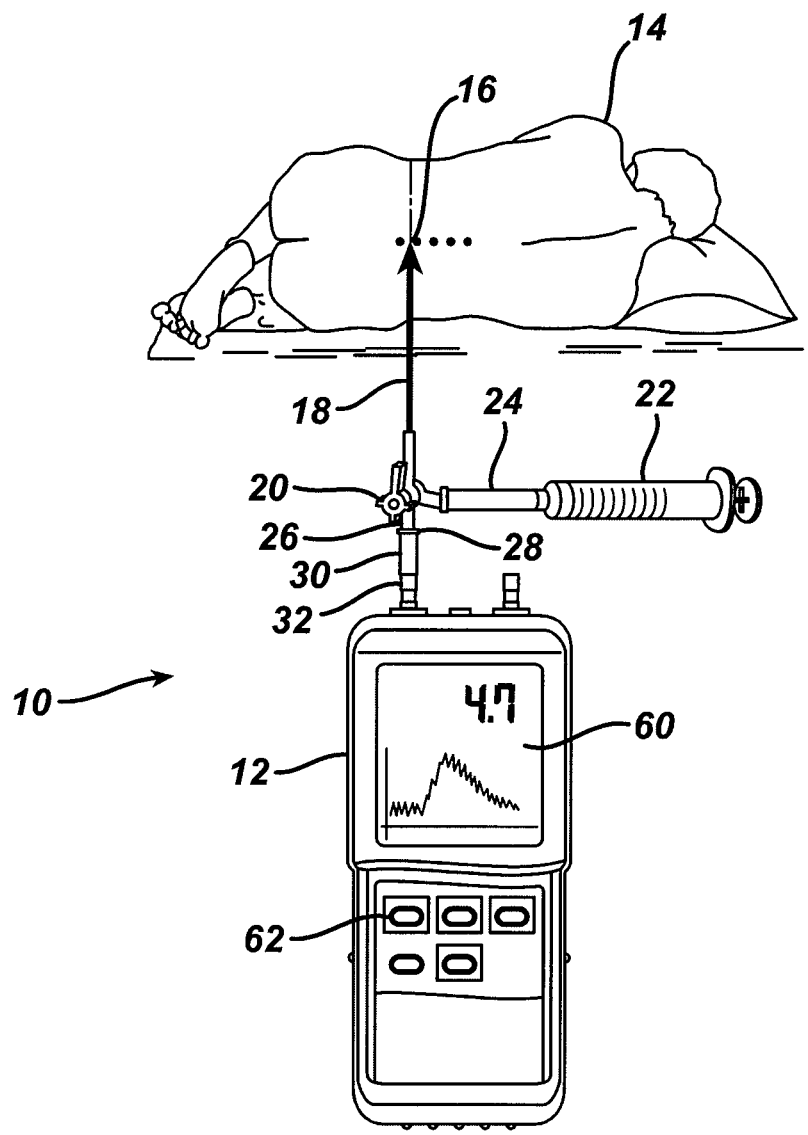
FIG. 1 illustrates a system of the invention for measuring a pressure of a fluid system in a patient.

A system 10 representative of one embodiment of the invention is presented in FIG. 1 as including a pressure sensor component 12 with integrated fluid dynamics assessment that can be coupled with a patient's 14 CSF system to measure and analyze the patient's CSF pressure, as well as methods for doing the same. As shown, the system is coupled to the patient's CSF system at a puncture site 16 which may represent a conventional lumbar tap. Tubing 18 fluidically couples the puncture site to a coupling element 20—in the illustrated embodiment, a three-way stopcock. The three-way stopcock 20 couples tubing 18 with syringe 22 (through tubing 24) and a first chamber 26. First chamber 26 is separated from a second chamber 30 by a membrane 28 (internal to the system illustrated in FIG. 1) that is movable to allow pressure from a fluid in the first chamber to be transmitted to fluid in the second chamber. Second chamber 30 is in fluid communication with pressure sensor port 32 of pressure sensor component 12 where a pressure sensor of the pressure sensor component can measure the pressure of a fluid in the second chamber for analysis and display. Accordingly, system 10 can measure the pressure of fluid in the patient's CSF system by way of the fluid and pressure communication sequence from puncture site 16 to pressure sensor port 32.

Figure 2:
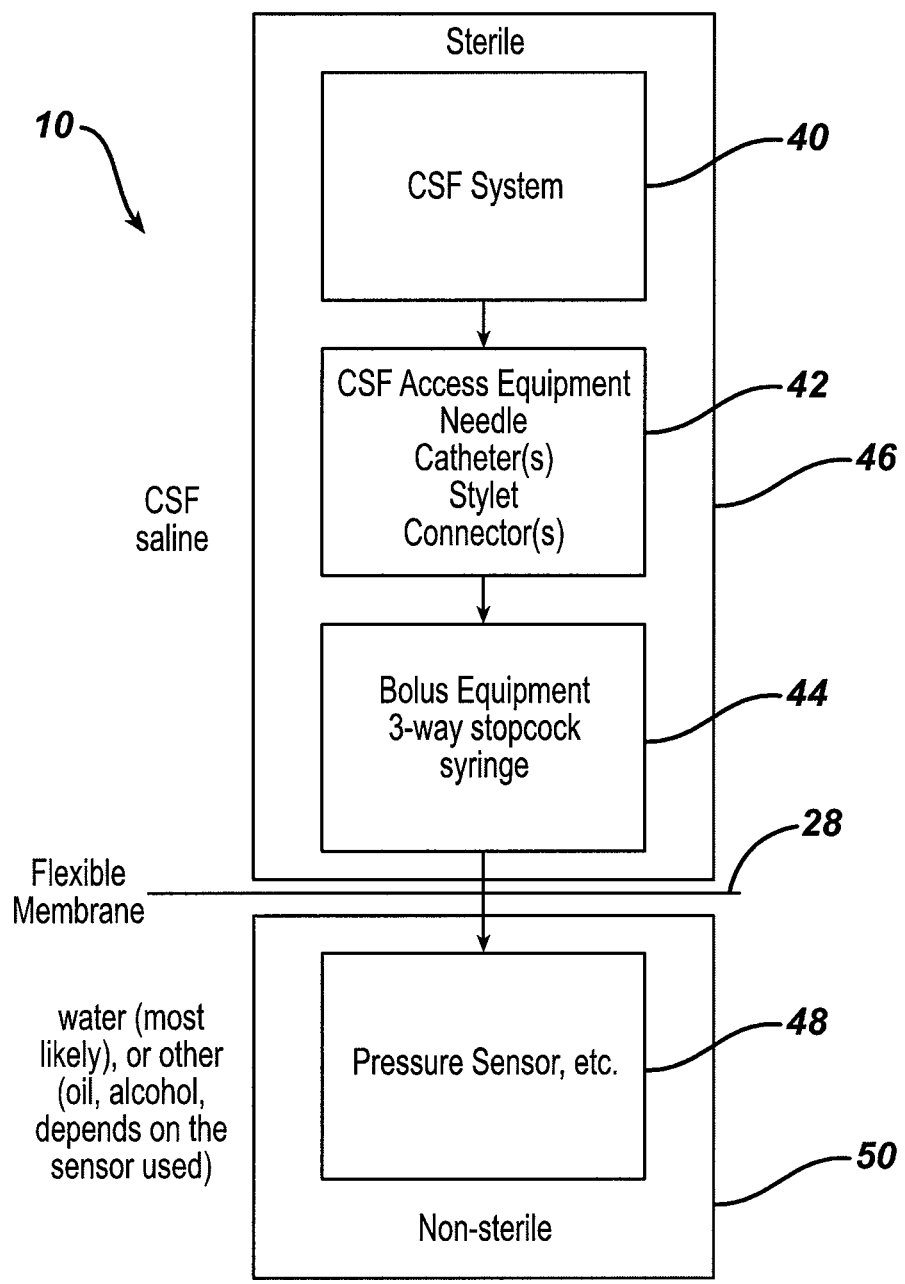
FIG. 2 is diagrammatic view illustrating additional features of the system of FIG. 1.

System 10 can be further described by reference to FIG. 2 which illustrates diagrammatically the system of FIG. 1. The patient's CSF system is illustrated by functional block 40 which is fluidically coupled to CSF Access Equipment 42. The CSF Access Equipment includes the elements necessary to tap into the patient's CSF system and provide access to that system outside of the patient's body. As noted above, this access is typically gained through a lumbar tap in which a large gage needle is used to access the CSF system in the space between the patient's vertebrae, often between the third and fourth lumbar vertebrae. As suggested in the Figure, however, this access could be gained using any variety of needle, catheter, stylet and/or connectors as might be appropriate for accessing the patient's CSF system. Further, if a system of the invention is deployed for use with a different fluid system of the patient, a person skilled in the art will recognize that access equipment suitable for coupling to that fluid system can be used within the spirit of the invention.

CSF Access Equipment 42 can be fluidically coupled to Bolus Equipment 44 if desired for manipulation of the fluid within the system. The Bolus Equipment typically includes a syringe for the injection and/or withdrawal of fluid from the system. A three-way stopcock can also be employed to control the flow of fluid. A person of skill in the art will recognize that other equipment may be used, a bi-directional or infusion pump for example, to inject or withdraw fluid from the system.

The elements so far described by reference to FIG. 2 fall within a sterile portion 46 of system 10. As these elements are exposed within the patient by virtue of the flow of fluid within the system, these element should be sterile as is well known in the art. The fluid flowing within the sterile portion of system 10 will generally include fluid from the patient's system being measured, in the illustrated embodiment CSF, and can also include other biocompatible fluids such as saline. Such biocompatible fluids can be used within the syringe to provide a bolus. Further, where fluidic coupling is long, especially between CSF Access Equipment 42 and Bolus Equipment 44 so as to make the positioning of the Bolus Equipment and the pressure sensor component more convenient for use, at least portions of the system may be filled with saline prior to connection with the patient to minimize CSF volume loss.

The fluid in the sterile portion 46 of system 10 can be coupled through membrane 28 to the pressure sensor 48. In general, pressure sensor 48 will reside in a non-sterile portion 50 of system 10 as it is likely to be re-used from patient to patient and the system can be constructed so as to separate the non-sterile portion from contact with the patient's fluids. Typical high accuracy pressure sensors require fluid coupling, such that there is a vetted surface on the sensor. This sensor is often located in a protected area within a lumen that is not easily accessed (e.g., within pressure sensor port 32). The pressure sensor lumen can be filled with water (or other liquids such as oil or alcohol depending on the particular sensor embodiment used) for this purpose. Membrane 28 can be located so as to contact fluid in the sterile region 46 on one side, and fluid in the non-sterile region 50 on the other. Where membrane 28 is movable or flexible, changes in fluid pressure in the sterile portion of the system (including the patient's CSF system) are transmitted by movement of the membrane to the fluid in the non-sterile portion 50. These pressures can be read by pressure sensor 48.

A pressure sensor component 12 for use with the invention can further be described by reference to FIG. 3. Pressure sensor component 12 can be a known hand-held fully integrated pressure sensor having a digital processor that can be configured to analyze the pressure signals provided in accordance with the description of FIGS. 1 and 2 above. Such known pressure sensors could include, for example, the Dwyer Instruments Series 477 handheld digital manometer available from Dwyer Instruments, Inc. of Michigan City, Ind., or the Fluke Model 717 or 718 pressure calibrators available from Fluke Corporation of Everett, Wash. Pressure sensor component 12 includes pressure sensor port 32, and also a second pressure sensor port 64 for pressure differential measurements. This second port can remain exposed to the atmosphere if it is not otherwise used. Pressure sensor component 12 also includes a display 60 for displaying pressure measurement results and analysis, and user input elements, buttons 62, for operating the component.

Figure 3:
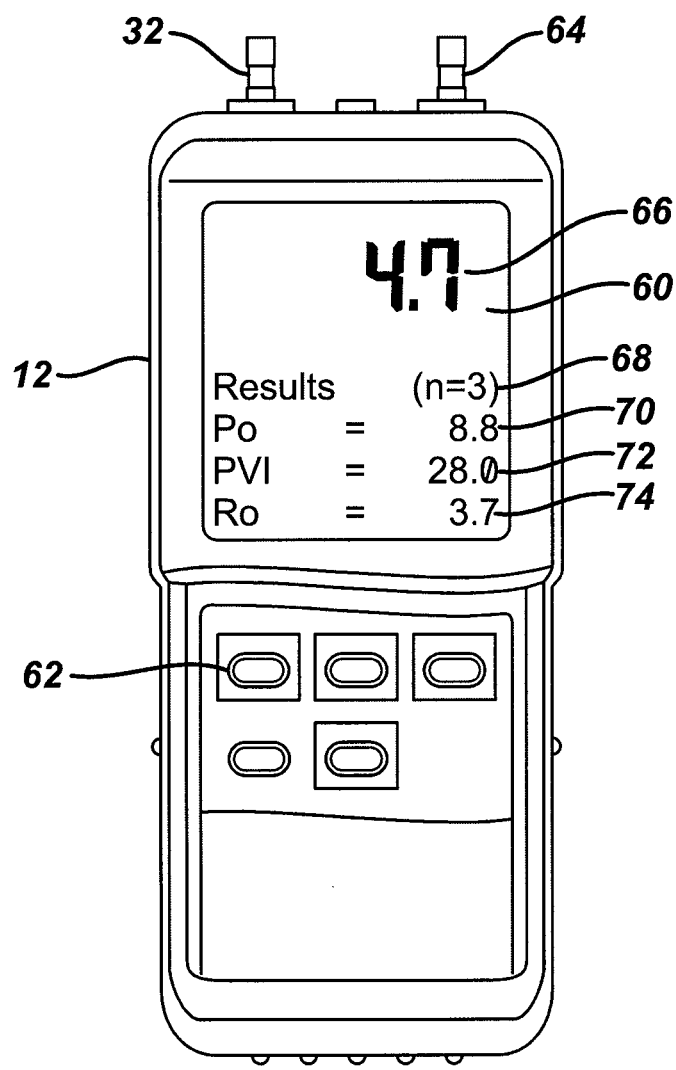
FIG. 3 illustrates a pressure sensor component of the invention.

Display 60 in FIG. 1 illustrates a graphical display of pressure measurements over time, while display 60 in FIG. 3 illustrates the current pressure 66 along with calculated values for the resting, baseline or starting pressure (Po) 70, the pressure-volume index (PVI) 72, and resistance to outflow (Ro) 74. The results are indicated to be for a third iteration (n=3) 68 of measurements. These CSF pressure dynamics testing results can yield information that can be used to confirm the probable diagnosis of Normal Pressure Hydrocephalus and aid in the selection of a shunt opening pressure for a shunt to be implanted in the patient.

While the illustrated display shows outflow resistance and pressure-volume index values, and exemplary methods for calculating and using these values are described below, the invention described herein is not limited to this choice of parameters or particular methods of calculation. Pressure sensor component 12 can be programmed to calculate other pressure based parameters and also to calculate the aforementioned parameters in ways other than those disclosed herein.

In fact, clinicians or researchers could develop new parameters to more accurately diagnose NPH or other fluid system abnormalities, the analysis of which using the systems and methods described herein is believed to fall within the present invention. In one embodiment of the present invention, pressure sensor component is programmable so as to allow a user to program the calculation of the user's own preferred parameters or to carry out the calculations using the user's preferred methods of calculation. Further information relating to the relationship between CSF abnormalities and pressure related parameters can be found in Shapiro K, Marmarou A, Shulman K, *Characterisation of clinical CSF dynamics and neural axis compliance using the pressure-volume index*, Annals of Neurology 7 (6) 508-514 (June 1980), which is incorporated herein by reference.

The resting pressure, $P_o$, can provide general information that may be used as an indicator for shunt opening pressure selection; its value can also used in further calculations as described below. The PVI can be calculated from the pressure change resulting from a rapid injection or withdrawal of fluid from the CSF space and has found widespread use both clinically and experimentally as a measure of lumped craniospinal compliance. The outflow resistance, $R_o$, has been shown to be a good indicator of patents who will benefit from CSF shunting. In general, normal values for $R_o$ are generally about 1.5 to 4 nm mmHg/ml/min, while patients suffering from NPH generally have $R_o$ values of about 4 to 12.

Figure 4:
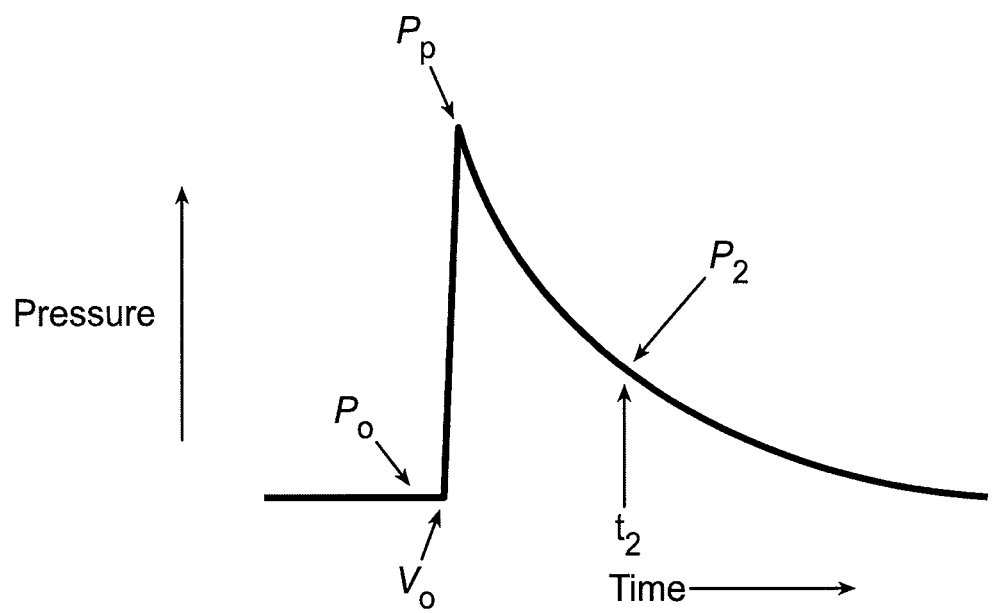
FIG. 4 illustrates a pressure graph used to illustrate calculations made by the pressure sensor of FIG. 3.

One exemplary approach to calculating these values using system 10 of FIG. 1, including pressure sensor component 12 as further illustrated in FIG. 3, can further be described by reference to FIG. 4. FIG. 4 provides a graph of pressure versus time that represents the patient's CSF pressure over time including the pressure response of the patient's CSF system to a bolus injection. The resting pressure, $P_o$, can be seen on the graph at a time before the bolus injection. At a given time, a bolus of volume $V_o$ is added to the system, for example using the syringe 22 of FIG. 1. The bolus injection results in a sharp rise in pressure reaching a peak pressure of $P_p$. The pressure drops over time from its peak and can be measured at a time $t_2$, typically two minutes after bolus injection, to generate a pressure reading $P_2$ that is indicative of the return trajectory of the patient's CSF pressure.

With these variables known, the patient's pressure-volume index can be calculated as follows:

$$PVI = V_o/\mathrm{Log}(P_p/P_o)$$

and the CSF outflow resistance can be calculated as:

$$R_o = t_2 \times P_o / PVI \times \mathrm{Log}\{(P_2/P_p)(P_p-P_o)/(P_2-P_o)\}$$

As noted above, the bolus injection, measurements and calculations may be performed in multiple iterations, with either individual iterations or mean values. In one embodiment, a user can select iterations for averaging, leaving out any apparently abnormal data.

Pressure sensor component 12 can also provide user defined variables. For example, the following variables with the following exemplary default values can be set:

| | |
|---|---|
| Infusion Volume | 4 cc |
| Recovery Time | 180 sec |
| PVI Limit | 13 ml |
| $P_o$ Limit | 30 mmHg |
| $P_p$ Limit | 30 mmHg |

These values/limits can be user adjustable to conform to particular circumstances.

Pressure sensor component 12 can also be configured to prompt a user through a measuring procedure. For example, with the pressure sensor component powered on, the user defined variables set as desired, and the system connected to a patient as illustrated in FIG. 1, the component will begin by displaying the resting pressure $P_o$. Once $P_o$ is recorded, the pressure sensor component can prompt the user to infuse the system with a measured volume of fluid. The user can then begin the infusion, typically by infusing 4 cc of saline at approximately 1 cc/sec. The user can watch the real-time pressure display to confirm the absence of anomalous peaks during infusion. Once the infusion is complete and $P_p$ is recorded, the pressure sensor component can prompt the user to wait, typically for three minutes or until the current pressure is less than $P_o$ plus 2 mmHg, while the component measures $P_2$. The pressure sensor component can then calculate $P_o$, PVI, and $R_o$ for that iteration and display them to the user. Once the pressure reading has recovered from the infusion, the pressure sensor component can prompt the user to perform another iteration or disconnect the system from the patient. The user can select iterations to include or exclude from mean calculations, and mean values can be calculated and displayed.

The pressure sensor component 12 illustrated in FIGS. 1 and 3 is shown as an integral handheld unit having a pressure sensor located within pressure sensor port 32, and all of the digital electronic components required to perform the calculations described above. A person skilled in the art will understand, however, that other configurations are possible. For example, the pressure sensor port 32, or only the sensor itself, could be fluidically coupled to second chamber 30 while maintaining electronic communication to a digital processing unit for performing desired display and calculation based on the pressure signal. Still further, the pressure sensor could be provided as part of the sterile portion 46 of system 10, making second chamber 30 unnecessary.

Accordingly, the embodiments of the present invention are not limited by what has been particularly shown and described, except as indicated by the appended claims. All publications and references cited herein are expressly incorporated herein by reference in their entirety.

What is claimed is:

1. A pressure sensor component comprising:
   a pressure sensing port for containing a fluid for pressure sensing; and
   a pressure sensor for measuring a pressure of the fluid in the pressure sensing port, wherein the pressure measured is indicative of a patient's cerebrospinal fluid pressure;
   wherein the pressure sensor component includes a digital processor in electrical communication with the pressure sensor, the pressure sensor component being configured to calculate at least two selected from the group consisting of resting pressure, outflow resistance, and pressure volume index based on the cerebrospinal fluid pressure.

2. The pressure sensor component of claim 1, wherein the pressure sensor component includes a display.

3. The pressure sensor component of claim 2, wherein the pressure sensor component is configured to display a graph of fluid pressures sensed over time.

4. The pressure sensor component of claim 1, wherein the pressure sensor component is configured to calculate at least one selected from the group consisting of resting pressure, outflow resistance, and pressure volume index in multiple iterations with selective calculation of mean results.

5. The pressure sensor component of claim 1, wherein the pressure sensor component is configured to calculate each of a resting pressure, an outflow resistance, and a pressure volume index.

6. The pressure sensor component of claim 1, wherein the pressure sensor component is an integral, hand-held component.

7. The pressure sensor component of claim 6, further comprising a pressure transmission medium in fluid contact with the pressure sensing port.

8. The pressure sensor component of claim 7, wherein the pressure transmission medium is a liquid.

9. The pressure sensor component of claim 8, wherein the liquid is other than cerebrospinal fluid.

10. The pressure sensor component of claim 6, further comprising a catheter connected to the pressure sensing port.

11. The pressure sensor component of claim 10, wherein the catheter includes a membrane that divides the catheter into a first chamber in fluid contact with the pressure sensing port and a second chamber fluidically connectable with a patient's cerebrospinal fluid system, the membrane transmitting fluid pressure from the second chamber to the first.

12. The pressure sensor component of claim 11, wherein the first chamber is filled with a liquid.

13. The pressure sensor component of claim 10, wherein the catheter includes a port for adding a liquid bolus to a patient's cerebrospinal fluid system.

14. The pressure sensor component of claim 13, wherein the port is a three-way stopcock.

15. The pressure sensor component of claim 2, wherein the pressure sensor component includes at least one button for operating the component.

16. The pressure sensor component of claim 15, wherein the processor is configured to calculate at least one selected from the group consisting of outflow resistance and pressure volume index.

17. The pressure sensor component of claim 16, wherein the pressure sensor component is configured to prompt a user through a sequence of measurement steps, the measurement steps including the injection of a bolus into the fluid system being measured.

18. The pressure sensor component of claim 17, wherein the pressure sensor component is configured to prompt a user to infuse the fluid system being measured with a measured volume of fluid.

19. The pressure sensor component of claim 18, wherein the pressure sensor component is configured to prompt a user to wait for a predetermined amount of time.

20. The pressure sensor component of claim 18, wherein the pressure sensor component is configured to prompt a user to wait for a predetermined pressure reading.

21. The pressure sensor component of claim 18, further comprising a catheter connected to the pressure sensing port.

22. The pressure sensor component of claim 21, wherein the catheter includes a port for adding a liquid bolus to a patient's cerebrospinal fluid system.

23. The pressure sensor component of claim 1, wherein the pressure sensor component is configured to calculate the pressure volume index (PVI) as a pressure change resulting from a rapid injection or withdrawal of a bolus fluid from a patient's CSF space.

24. The pressure sensor component of claim 23, wherein the pressure sensor component is further programmed configured to calculate the PVI as:

$$PVI = V_o / \text{Log}(P_p/P_o)$$

where:
$V_o$ is the volume of the bolus;
$P_o$ is the resting pressure; and
$P_p$ is the peak pressure resulting from the addition of the bolus.

25. The pressure sensor component of claim 1, wherein the pressure sensor component is programmed configured to calculate the outflow resistance ($R_o$) as indicative of a return trajectory of a patient's CSF pressure following the addition of a bolus fluid to a patient's CSF space.

26. The pressure sensor component of claim 25, wherein the pressure sensor component is further configured to calculate $R_o$ as:

$$R_o = t_2 \times P_o / PVI \times \text{Log}\{(P_2/P_p)(P_p-P_o)/(P_2-P_o)\}$$

where:
$t_2$ is a measured time;
$P_o$ is the resting pressure;
PVI is the pressure volume index;
$P_2$ is a measured pressure reading at time $t_2$ after the bolus addition; and
$P_p$ is the peak pressure resulting from the addition of the bolus.

* * * * *